US007319037B1

(12) United States Patent
Albeck-Marom

(10) Patent No.: US 7,319,037 B1
(45) Date of Patent: Jan. 15, 2008

(54) FLUID TESTER AND METHOD OF USE

(76) Inventor: Orit Albeck-Marom, 34/2 Kisufim Street, Tel Aviv (IL) 69355

( * ) Notice: Subject to any disclaimer, the term of this patent is extended or adjusted under 35 U.S.C. 154(b) by 0 days.

(21) Appl. No.: 10/145,797

(22) Filed: May 14, 2002

(51) Int. Cl.
*G01N 33/18* (2006.01)
(52) U.S. Cl. .................... 436/39; 436/163; 422/58; 422/61
(58) Field of Classification Search ................ 422/58, 422/61; 436/39, 163
See application file for complete search history.

(56) References Cited

U.S. PATENT DOCUMENTS

| | | | |
|---|---|---|---|
| 2,929,687 A | 3/1960 | Buchoff | |
| 3,381,572 A | 5/1968 | Tuwiner | |
| 3,443,903 A | 5/1969 | Haack et al. | |
| 3,510,263 A | 5/1970 | Hach | |
| 3,773,425 A | 11/1973 | Bentley | |
| 3,876,378 A | 4/1975 | Montagnon | |
| 3,891,507 A * | 6/1975 | Breuer | 435/14 |
| 3,992,158 A * | 11/1976 | Przybylowicz et al. | 422/57 |
| 4,125,376 A | 11/1978 | Razulis | |
| 4,126,417 A * | 11/1978 | Edwards | 422/56 |
| 4,180,009 A * | 12/1979 | Voss et al. | 116/206 |
| 4,409,182 A * | 10/1983 | Macklem | 422/61 |
| 4,663,126 A * | 5/1987 | Gould et al. | 422/58 |
| 4,797,256 A * | 1/1989 | Watlington, IV | 422/58 |
| 4,877,580 A * | 10/1989 | Aronowitz et al. | 422/58 |
| 4,904,605 A | 2/1990 | O'Brien et al. | |
| D308,833 S | 6/1990 | Mowka, Jr. | |
| 4,960,565 A * | 10/1990 | Shurben | 422/61 |
| 4,962,025 A * | 10/1990 | Moldowan | 435/25 |
| 5,710,372 A * | 1/1998 | Becket | 73/53.01 |
| 5,904,898 A | 5/1999 | Markart | |

* cited by examiner

*Primary Examiner*—Lyle A. Alexander
(74) *Attorney, Agent, or Firm*—Edward Langer; Shiboleth, Yisraeli, Roberts, Zisman & Co.

(57) ABSTRACT

Fluid testing device for determining the value of each of a plurality of properties of a fluid, the fluid testing device including a planar base and a plurality of test sections, located on the planar base, each of the test sections including a test sub-section which exhibits a color according to the value, as a result of reaction of a reagent with the fluid and a reference section located adjacent to the test sub-section, the reference section including a plurality of different reference colors.

38 Claims, 10 Drawing Sheets

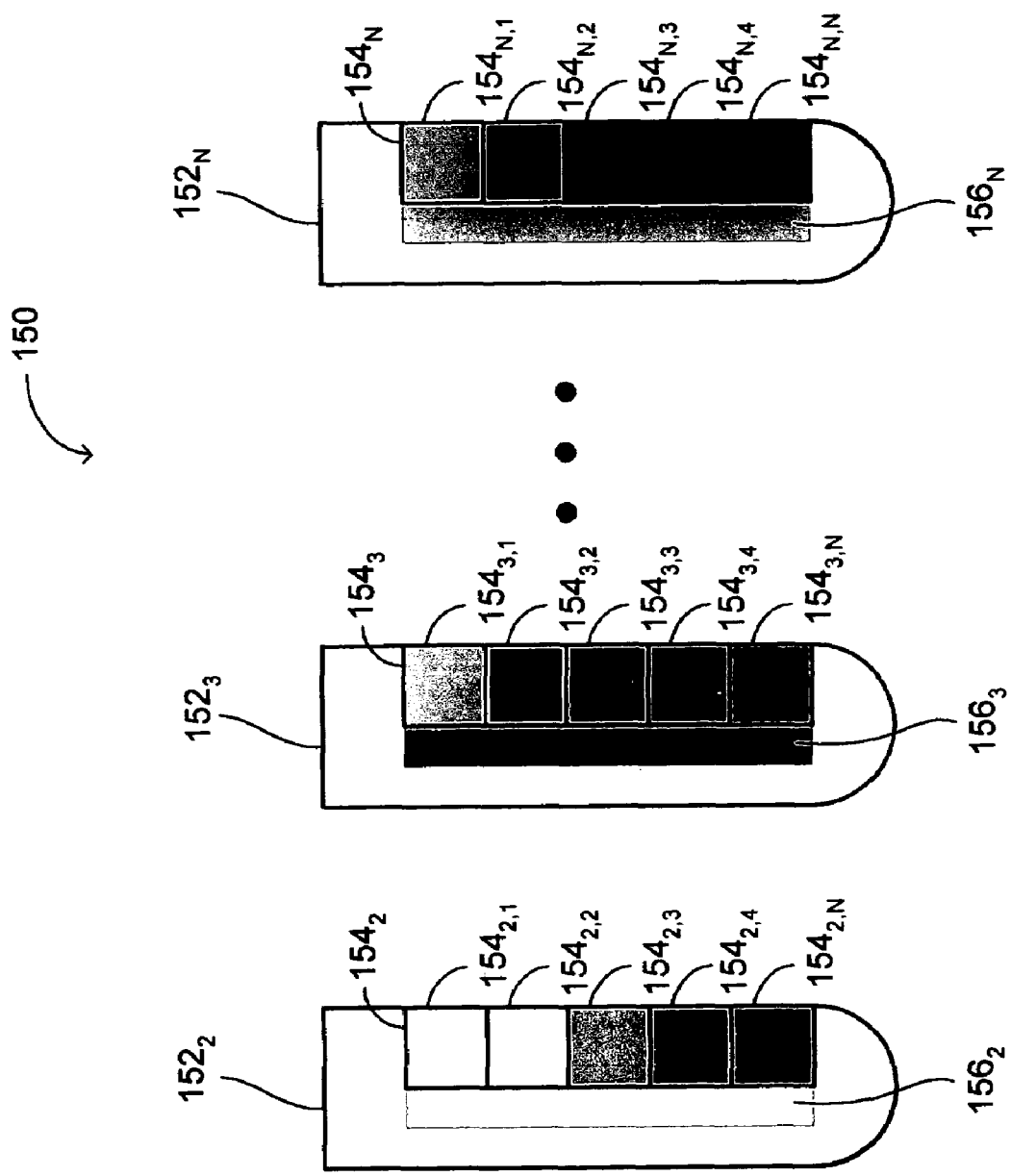

FLUID TESTER AND METHOD OF USE

FIELD OF THE DISCLOSED TECHNIQUE

The disclosed technique relates to methods and systems for testing fluids in general, and to methods and systems for testing water, in particular.

BACKGROUND OF THE DISCLOSED TECHNIQUE

Systems and methods for testing water for chemicals and other properties are known in the art. A prevalent method consists of inserting into the tested water an absorbent material, such as paper, which is impregnated with a chemical reagent. The reagent chemical is designed to react with predetermined chemicals or predetermined fluid properties. As a result of this reaction, the color of the reagent chemical changes, and this is visible on the absorbent material. Accordingly, a color change is achieved when the water under test, contains these predetermined chemicals or is characterized by the predetermined fluid properties. The hue of the resulting color can further quantitatively determine the level of the detected chemical or property, by comparing the hue with a standard color scale.

U.S. Pat. No. 3,876,378 to Montagnon, entitled "Analytic Device Utilizing Reaction-Sensitive Chemical Product", is directed to an apparatus for chemical testing of liquids using a chemical reagent. The construction of this apparatus is intended to overcome some of the problems that may occur in such tests. The apparatus includes a vessel with a flange at its bottom forming a groove, and a disc made of absorbent material, which comfortably fits inside the groove. The disc is impregnated with a chemical reagent, so that upon introduction of the tested liquid, the disc may undergo a color change, depending on the conditions of the liquid.

U.S. Pat. No. 4,904,605 entitled "Method and Apparatus for Residential Water Test Kit" issued to O'Brien et al., is directed to a system and method for testing water for a plurality of chemicals and other characteristics. The water test kit includes a container with a label on the exterior. The label includes a color comparison chart and optionally, operating instructions. The color comparison chart indicates the properties to be tested. Each row of the chart pertains to one chemical or property, and includes a scale of colors and their corresponding levels of the chemical concentration or the property. The kit further includes a dipstick or test strip. The dipstick or test strip is divided into a plurality of areas. Each area contains a reagent that reacts to a specific chemical or fluid property, producing a color change in that area. To test the water using this device, the user first fills the bottle with tap water. She then fully immerses the test strip in the sample bottle and waits for 30 seconds. Next, she removes the test strip from the water, and positions the test strip so that it is aligned with the color chart. Finally, she compares the color of each of the test strip areas to the corresponding section of the chart.

Numbers indicating problematic levels are underlined and may also be printed in a different color (e.g., red) from the rest of the numbers on the chart. A solution chart may also be provided, on which solutions to the problems are given, possibly by reference to different water filters and the like. The need for the strip to be matched with the color chart makes this system relatively complicated to operate, and may result in misreadings or other errors by the unskilled user. It is also necessary for all of the separate parts of the kit to be present in order for the testing to be possible.

Another method for colorimetric testing of water known in the art consists of inserting a reagent into the water sample and allowing it to react inside the water, thus causing the water to change color, and then comparing the color of the water with a standard color scale.

U.S. Pat. No. 3,381,572 entitled "Colorimetric Testing Device" issued to Tuwiner, is directed to a device for quantitatively determining the concentration of a chemical or the levels of a property such as pH. The apparatus includes an optical color index unit, adjacent to a container for the tested sample. The index unit color changes gradually from one end to another, in correspondence with the color change of the tested sample at different levels of the property being tested. The index unit also has numbers printed thereon to indicate the corresponding levels. To perform the test, the user inserts the sample, together with a color-indicating reagent, into the container and compares the changed color of the sample with the index unit color scale.

U.S. Pat. No. 4,125,376 entitled "Method for Detecting Water Pollutants" issued to Razulis, is directed to a method for identifying chemicals in water. The apparatus is a transparent container, with an urethane foam cube disposed therein, and a plug for sealing the tube. The urethane foam cube is impregnated with a specific spot detection chemical. The chemical produces a calorimetric indication when exposed to specific pollutants in the tested water sample. The method is carried out by adding the water to the container, sealing the container with a plug and then shaking it. The color change is then compared to a color comparator chart of the specific pollutants.

U.S. Pat. No. 4,180,009 issued to Voss et al., and entitled "Ion Concentration Testing Apparatus", is directed to a device for determining different ion concentrations in swimming pool water. The device includes two measurement containers, a reference container and an indicating screen. The measurement containers and the reference container are bounded on one side by a common wall. The indicating screen is located in front of the common wall and includes a plurality of indicating windows associated with the measurement containers and a plurality of indicating windows associated with the reference container. The measurement containers and the reference container are arranged in a row and each has a square or a rectangular cross section. The indicating windows are distributed over the height of the measurement containers and the reference container. Each of the indicating windows associated with the reference container, has a reference or standard coloration corresponding to a predetermined ion concentration. The indicating windows are transparent.

The indicating screen further includes a plurality of marks adjacent to the indicating windows associated with the measurement containers. The value of each of the marks is related with the respective indicating window associated with the reference container. The user fills the measurement containers with water and inserts different color forming reagents, according to the particular ion concentration to be tested, in each measurement container. The color forming reagents dissolve and the water in each measurement container acquires a color which corresponds with the concentration of the ion. The user compares the color of the water seen through the indicating windows associated with a measurement container, with the respective reference coloration of the indicating window associated with the reference container. The user determines the ion concentration by reading the value of the mark, which corresponds with the reference coloration which was identified as a result of this comparison.

Merck KGaA located in Darmstadt, Germany, discloses a first method for determining the concentration of substances in water, landfills and soil. According to the first method, the user adds a liquid reagent to a liquid sample, thereby rendering a color to the liquid. The concentration of the substance is measured by a photometer, according to the color of the liquid. Merck KGaA discloses a second method for testing a solution. According to the second method, the user dips a test strip in the solution. After a given reaction time has elapsed, the user compares the color of the reaction zone with a color scale on the package, thereby determining the concentration.

Merck KGaA discloses a system for determining the concentration of substances or a parameter in a liquid. The system includes an electronic instrument, a plurality of test strips and a bar code. Each of the test strips are designated to test the concentration of a selected substance or a selected parameter in the liquid. The bar code includes information respective of the selected substance or the selected parameter. The user calibrates the electronic instrument, by passing the bar code through the electronic instrument. The user then dips a test strip in the liquid, whereby the reaction renders a color to the test strip. The user passes the test strip through the electronic instrument, the electronic instrument determines the value of the concentration or the parameter and displays this value on a display.

Hach Company located in Colorado, U.S.A., discloses a colorimetric method for determining the concentration of a parameter in a sample. The user adds a reagent to the sample, thereby rendering a color to the sample. The user determines the concentration by comparing the color of the sample with test strips, color cubes, color discs, a colorimeter or a spectrometer. Hach discloses an electrochemical method for determining the concentration of a parameter. According to the electrochemical method, the presence or the absence of a parameter is determined, by measuring the electrical activity of a sample. Hach discloses a titration method for determining the concentration of a substance. According to the titration method, the user dispenses a reagent on the sample, until the color of the sample changes. The user determines the concentration by measuring the volume of the reagent which is dispensed (e.g., by counting the drops of the reagent dispensed from an eye dropper, or according to the reading of a digital titrator).

SUMMARY OF THE DISCLOSED TECHNIQUE

It is an object of the disclosed technique to provide a novel method and system for determining the properties of a fluid.

In accordance with the disclosed technique, there is thus provided an integrated, multi-test fluid testing device for simultaneously determining the value of each of a plurality of properties of a fluid. The fluid testing device includes a planar base and a plurality of test sections, located on the planar base. Each of the test sections includes a test sub-section and a reference section located adjacent to and in contact with the test sub-section, with the test sub-section being large enough to substantially encompass the entire reference section. Each test sub-section exhibits a reaction color according to the value, as a result of reaction of a reagent with the fluid. The reference section includes a plurality of different reference colors.

In accordance with another aspect of the disclosed technique, there is thus provided a fluid testing device for determining the value of each of a plurality of properties of a fluid. The fluid testing device includes a container, a plurality of test sections and a plurality of reference sections. Each container has at least one transparent portion. Each of the test sections exhibits a color according to the value, as a result of reaction of a reagent with the fluid. Each of the reference sections is located adjacent to a respective one of the test sections and each of the reference sections includes a plurality of different reference colors.

In accordance with a further aspect of the disclosed technique, there is thus provided a fluid testing device for determining the value of each of a plurality of properties of a fluid. The fluid testing device includes a plurality of containers, a test section for each of the containers and a reference section for each of the test sections. Each container has at least one transparent portion. Each test section exhibits a color according to the value, as a result of reaction of a reagent with the fluid. Each reference section is located adjacent to a respective test section, wherein the reference section includes a plurality of different reference colors.

In accordance with another aspect of the disclosed technique, there is thus provided a method for determining the value of a plurality of properties of a fluid. The method includes the procedures of providing a plurality of test sections on a planar base and pre-associating a multiple color reference scheme with a property test substance of a respective one of the test sections. The method further includes the procedures of matching a test color of the property test substance, with a selected one of different colors of the multiple color reference scheme and determining a respective one of the values according to the outcome of the procedure of matching.

In accordance with a further aspect of the disclosed technique, there is thus provided a method for determining the value of a plurality of properties of a fluid. The method includes the procedures of providing a plurality of test sections, each located on the inner wall of a respective one of a plurality of containers and pre-associating a multiple color reference scheme with a property test substance of a respective one of the test sections. The method further includes the procedures of matching a test color of the property test substance, with a selected one of different colors of the multiple color reference scheme and determining a respective one of the values according to the outcome of the procedure of matching.

BRIEF DESCRIPTION OF THE DRAWINGS

The disclosed technique will be understood and appreciated more fully from the following detailed description taken in conjunction with the drawings in which:

FIG. 2B is a schematic illustration of the containers of FIG. 2A, after reaction of a fluid with the test substance of the test sub-section of each container;

DETAILED DESCRIPTION OF THE EMBODIMENTS

The disclosed technique overcomes the disadvantages of the prior art by providing a test medium in which the color of the fluid changes as a result of reaction with a plurality of test substances, and the user determines a respective property of the fluid, by matching a respective resultant color with a respective color index. A battery of associated pairs of test sections and reference schemes can be placed side by side, such as on a card, whereby the user determines the concentration of different substances in the fluid, by immersing the card in the fluid and matching the color of the test section with the reference scheme. Each test section is impregnated with a selected substance, whereby the reaction of the selected substance with the fluid enables the user to determine the concentration of another selected substance in the fluid.

Figure 1A:
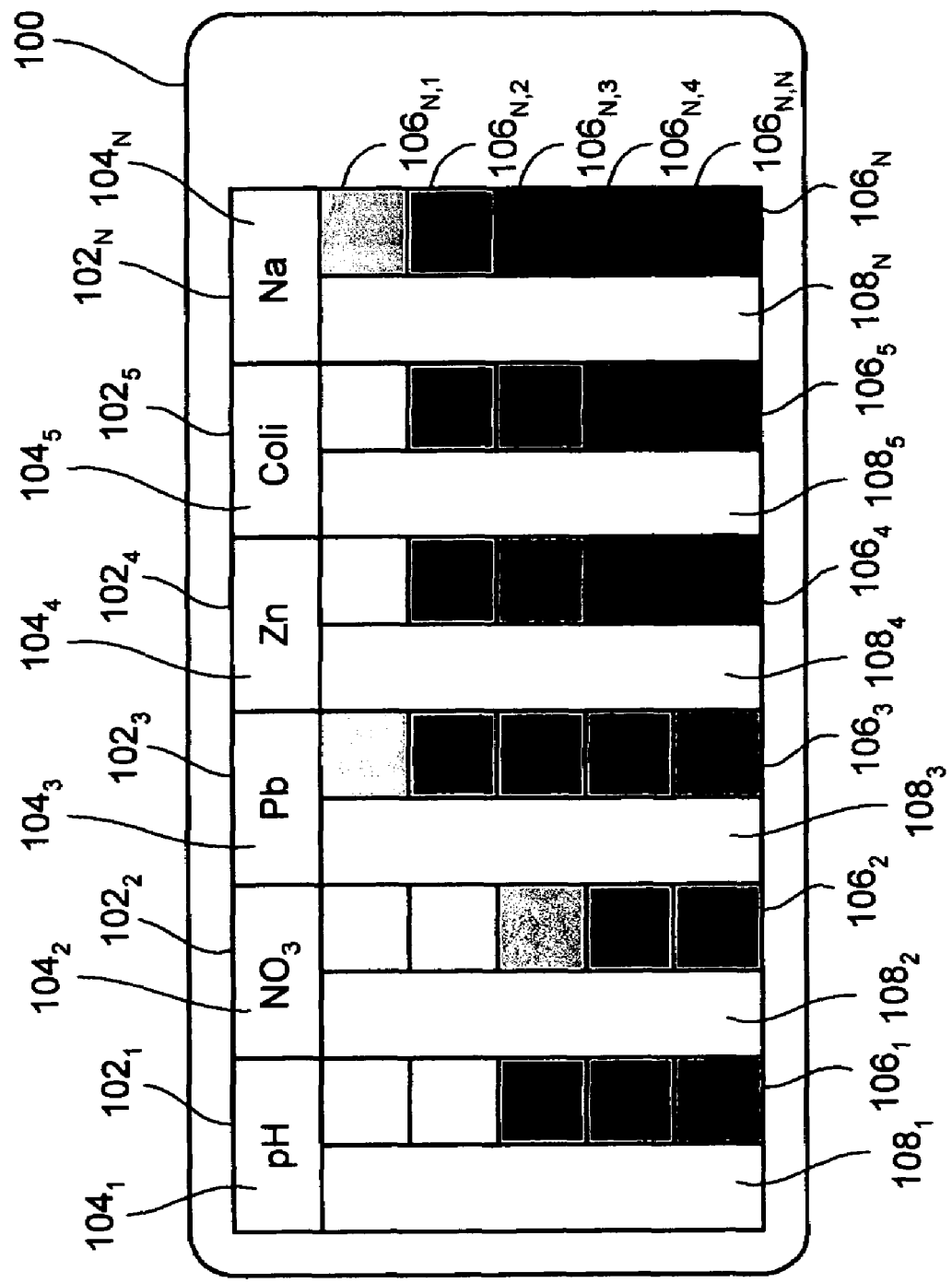
FIG. 1A is a schematic illustration of a fluid testing device, constructed and operative in accordance with an embodiment of the disclosed technique.
Figure 1B:
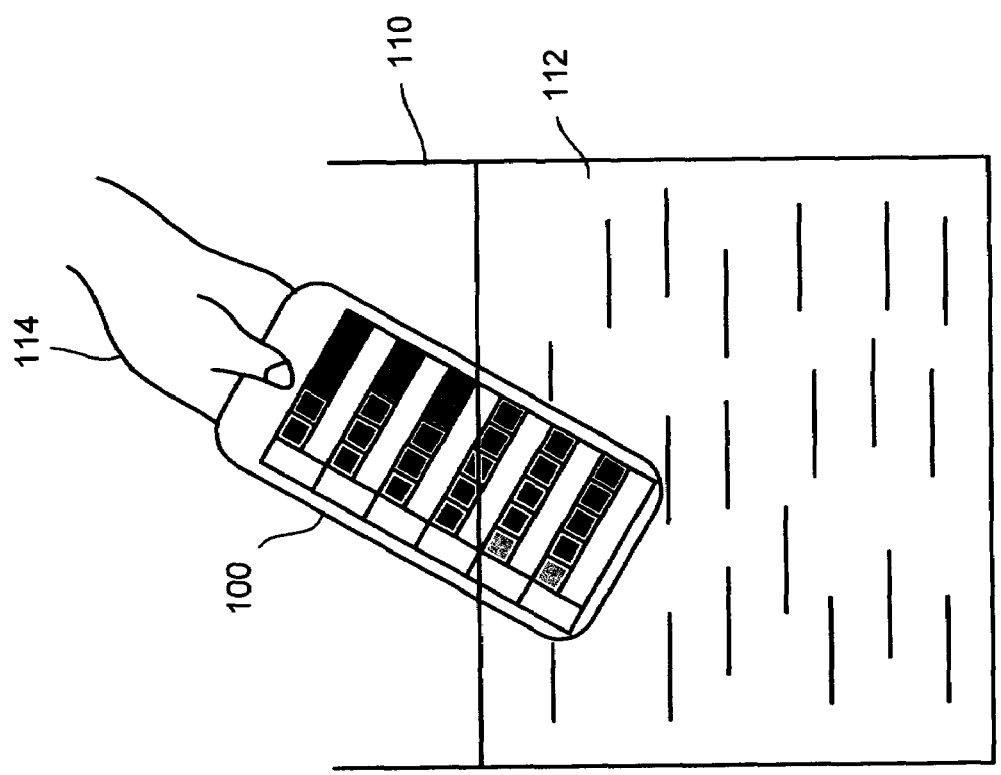
FIG. 1B is a schematic illustration of the fluid testing device of FIG. 1A being immersed in a fluid.
Figure 1C:
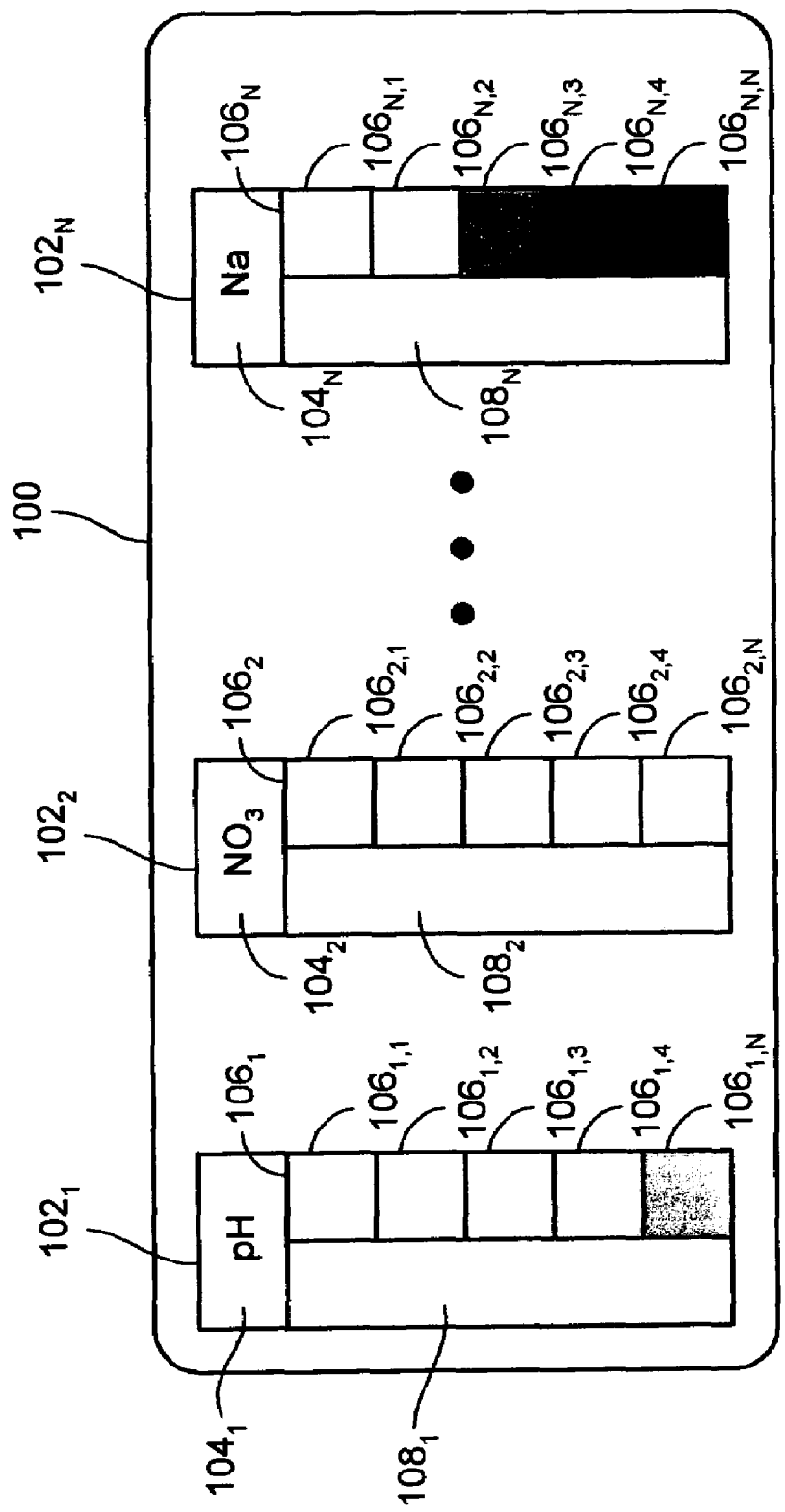
FIG. 1C is a schematic illustration of the fluid testing device of FIG. 1A, wherein the colors of the test sections have changed, after immersion of the fluid testing device in the fluid.

Reference is now made to FIGS. 1A, 1B and 1C. FIG. 1A is a schematic illustration of a fluid testing device, generally referenced 100, constructed and operative in accordance with an embodiment of the disclosed technique. FIG. 1B is a schematic illustration of the fluid testing device of FIG. 1A being immersed in a fluid. FIG. 1C is a schematic illustration of the fluid testing device of FIG. 1A, wherein the colors of the test sections have changed, after immersion of the fluid testing device in the fluid.

With reference to FIG. 1A, fluid testing device 100 includes a plurality of test sections $102_1$, $102_2$, $102_3$, $102_4$, $102_5$ and $102_N$. Test sections $102_1$, $102_2$, $102_3$, $102_4$, $102_5$ and $102_N$ include label sections $104_1$, $104_2$, $104_3$, $104_4$, $104_5$ and $104_N$, reference schemes $106_1$, $106_2$, $106_3$, $106_4$, $106_5$ and $106_N$, and test sub-sections $108_1$, $108_2$, $108_3$, $108_4$, $108_5$ and $108_N$, respectively. Each reference scheme further includes a plurality of reference colored sub-sections, each of which is in a different color. For example, reference scheme $106_N$ includes reference colored sub-sections $106_{N,1}$, $106_{N,2}$, $106_{N,3}$, $106_{N,4}$ and $106_{N,N}$, which are in different shades of blue. According to the example set forth in FIG. 1A, reference schemes $106_1$, $106_2$, $106_3$, $106_4$ and $106_5$ include reference colored sub-sections in different shades of brown, yellow, green, turquoise and purple, respectively.

Generally, a color can be defined according to a hue (e.g., blue, green, red, yellow, and the like), a saturation level and a brightness level. The saturation level defines the concentration of a specific hue. The brightness level defines the level of brightness or darkness of the hue. For example, a yellow oil paint consists of a mixture of linseed oil and lead chromate. The linseed oil allows the paint to flow and the lead chromate renders a yellow color to the oil paint. The saturation level of the yellow oil paint is defined by the amount of lead chromate in a given volume of linseed oil. The brightness level of the yellow oil paint is defined by the amount of white lead (for whiteness) or charcoal (for darkness) in the given volume of linseed oil.

It is noted that some or all of the reference colored sub-sections in a given test section can be in different hues (e.g., blue, green, red, yellow, and the like). Alternatively, all the reference colored sub-sections in a given test section can be in the same hue, but each having a different saturation level, brightness level, or both (e.g., each of the reference colored sub-sections of a given test section being a different shade of red).

Each of the label sections $104_1$, $104_2$, $104_3$, $104_4$, $104_5$ and $104_N$ indicates a property of the fluid or a substance in the fluid, whose concentration can be determined by matching the color of the respective test sub-section with the color of one of the reference colored sub-sections of the respective reference scheme. In the example set forth in FIG. 1A, $test section $102_1$ is constructed to test the pH of water and test sections $102_2$, $102_3$, $102_4$, $102_5$ and $102_N$ are constructed to test the concentration of nitrate ($NO_3$), lead (Pb), zinc (Zn), Escherichia Coli (E. Coli) and sodium (Na), respectively, in water. It is noted that sedimentation, the presence of general or specific bacteria, and concentration of hydrogen sulfide and nitrite ($NO_2$) can be determined. It is further noted that other tests for other substances in other fluids can also be imprinted on a card according to the disclosed technique, such as air, liquid fuel, crude oil, and the like.

Fluid testing device 100 is made of a material which substantially remains stable after being immersed in the fluid. For this purpose, fluid testing device 100 can be made of a flexible polymer, rigid polymer, glass, paper, plastic coated paper, cardboard, timber, dry clay, ceramic, masonry, leather, textile, metal, fabricated materials, and the like. Fluid testing device 100 is a substantially thin sheet in the form of rectangle, square, triangle, rhombus, parallelogram, trapezoid, quadrilateral, circle, annulus, ellipse, sector of a circle, freeform closed curve, and the like. Geometrically, the thin sheet is a plane which can either be flat or warped (i.e., rolled, folded, twisted, convex, concave, and the like).

Each test sub-section is impregnated with a test substance whose reaction with the fluid causes the color of the test sub-section to change, whereby the new color of the test sub-section indicates the concentration of a selected substance in the fluid or the concentration of a selected property of the fluid under test, such that the indication is provided in a recorded form.

With reference to FIG. 1B, a container 110 contains a fluid 112 which is to be tested. User 114 immerses fluid testing device 100 in the fluid 112 and waits for the test substances in each of the test sub-sections $108_1$, $108_2$, $108_3$, $108_4$, $108_5$ and $108_N$ to react with the fluid.

With reference to FIG. 1C, reference colored sub-sections $106_{1,1}$, $106_{1,2}$, $106_{1,3}$, $106_{1,4}$ and $106_{1,N}$ designate pH levels of 9, 8, 7, 6 and 5, respectively. Reference colored sub-sections $106_{2,1}$, $106_{2,2}$, $106_{2,3}$, $106_{2,4}$ and $106_{2,N}$ designate nitrate concentrations of 14, 12, 10, 8 and 6 milligram per liter (mg/l), respectively. Reference colored sub-sections $106_{N,1}$, $106_{N,2}$, $106_{N,3}$, $106_{N,4}$ and $106_{N,N}$ designate sodium concentrations of 16, 15, 14, 13 and 12 mg/l, respectively.

In the following description, fluid 112 is water. When fluid 112 reacts with the test substance which is impregnated in test sub-section $108_1$, the color of test sub-section $108_1$ changes to a hue which corresponds to the pH level of fluid 112. When fluid 112 reacts with the test substance which is impregnated in test sub-section $108_2$, the color of test sub-section $108_2$ changes to a hue which corresponds to the nitrate level of fluid 112. When fluid 112 reacts with the test substance which is impregnated in test sub-section $108_N$, the color of test sub-section $108_N$ changes to a hue which corresponds to the sodium level of fluid 112. User 114 reads the concentration of a selected substance in water, by matching the color of the test sub-section, with the color of one of the reference colored sub-sections of the respective reference scheme. It is noted that since the test sub-section color becomes substantially visually merged with the matching reference color, the matching process is a straight forward operation and that the user does not have to align the test sub-sections with the reference colored sub-sections.

For example, user 114 compares the color of test sub-section $108_1$ with reference colored sub-sections $106_{1,1}$, $106_{1,2}$, $106_{1,3}$, $106_{1,4}$ and $106_{1,N}$ and determines that the color of test sub-section $108_1$ is substantially similar to the color of reference colored sub-section $106_{1,3}$. Thus, user 114 determines that the pH of fluid 112 is 7. User 114 compares the color of test sub-section $108_2$ with reference colored sub-sections $106_{2,1}$, $106_{2,2}$, $106_{2,3}$, $106_{2,4}$ and $106_{2,N}$ and determines that the color of test sub-section $108_2$ is substantially similar to the color of reference colored sub-section $106_{2,4}$. Thus, user 114 determines that the concentration of nitrate in fluid 112 is 8 mg/l. User 114 compares the color of test sub-section $108_N$ with reference colored sub-sections $106_{N,1}$, $106_{N,2}$, $106_{N,3}$, $106_{N,4}$ and $106_{N,N}$ and determines that the color of test sub-section $108_N$ is substantially similar to the color of reference colored sub-section $106_{N,1}$. Thus, user 114 determines that the concentration of sodium in fluid 112 is 16 mg/l. It is noted that a substantially large number of test sections $102_1$, $102_2$ and $102_N$ can be constructed on fluid testing device 100, thus enabling the testing of a substantially large number of properties and substance concentrations in the fluid, simultaneously.

Figure 2A:
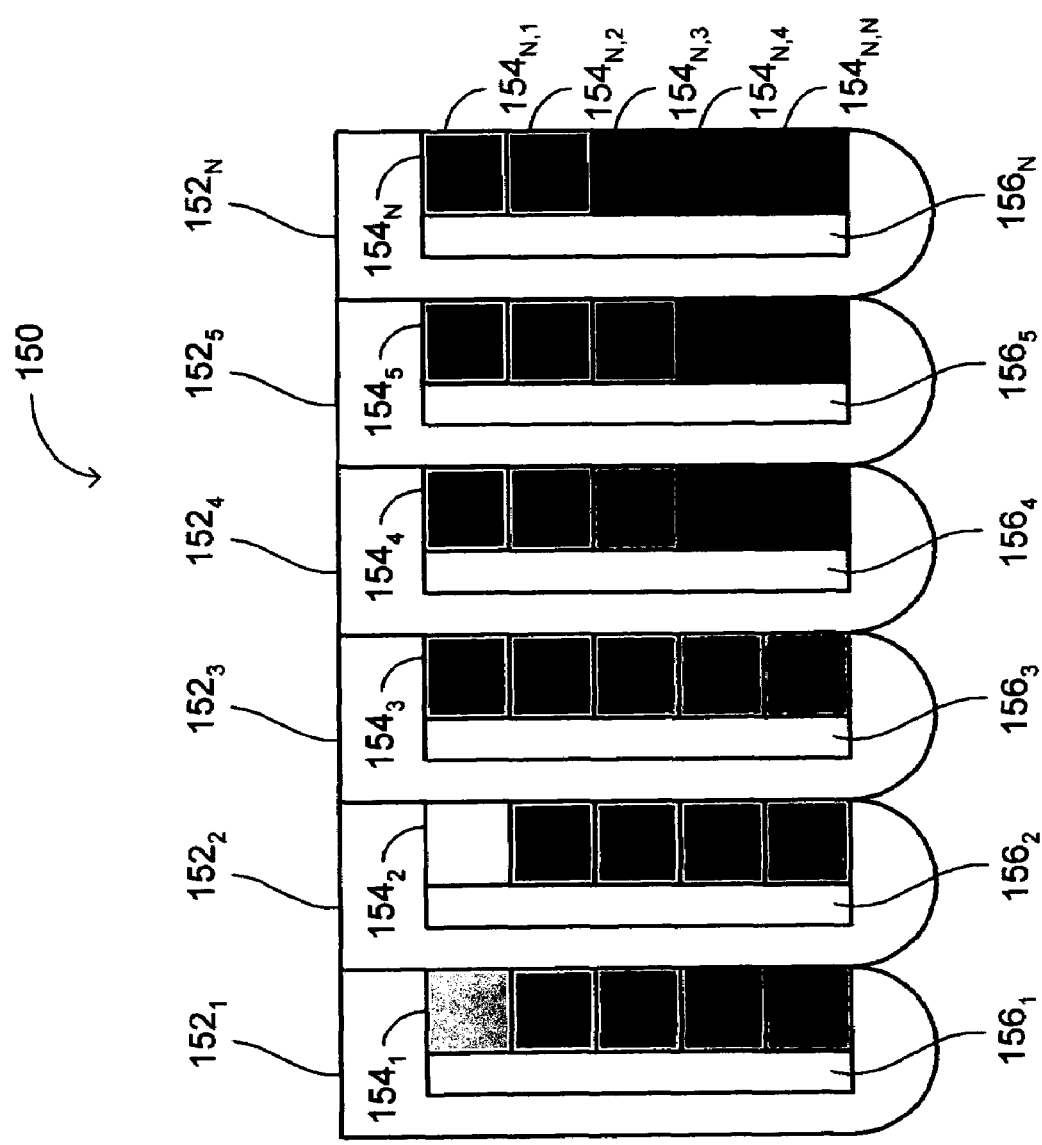
FIG. 2A is a schematic illustration of a battery of containers, constructed and operative in accordance with another embodiment of the disclosed technique.

Reference is now made to FIGS. 2A and 2B. FIG. 2A is a schematic illustration of a battery of containers, generally referenced 150, constructed and operative in accordance with another embodiment of the disclosed technique. FIG. 2B is a schematic illustration of the containers of FIG. 2A, after reaction of a fluid with the test substance of the test sub-section of each container.

The battery of containers 150, includes a plurality of containers $152_1$, $152_2$, $152_3$, $152_4$, $152_5$ and $152_N$. Each of containers $152_1$, $152_2$, $152_3$, $152_4$, $152_5$ and $152_N$ is constructed separately and are fastened together, by an adhesive, at least one fastener, welding, and the like. Alternatively, containers $152_1$, $152_2$, $152_3$, $152_4$, $152_5$ and $152_N$ are constructed as separate cavities within a single body.

Containers $152_1$, $152_2$, $152_3$, $152_4$, $152_5$ and $152_N$ include reference schemes $154_1$, $154_2$, $154_3$, $154_4$, $154_5$ and $154_N$ and test sub-sections $156_1$, $156_2$, $156_3$, $156_4$, $156_5$ and $156_N$, respectively. Each reference scheme further includes a plurality of reference colored sub-sections, each of which is in a different color. For example, reference scheme $154_N$ includes reference colored sub-sections $154_{N,1}$, $154_{N,2}$, $154_{N,3}$, $154_{N,4}$ and $154_{N,N}$, which are in different shades of blue. According to the example set forth in FIG. 2A, reference schemes $154_1$, $154_2$, $154_3$, $154_4$ and $154_5$ include reference colored sub-sections in different shades of brown, yellow, green, turquoise, purple and blue, respectively. Each of the test sub-sections $156_1$, $156_2$, $156_3$, $156_4$, $156_5$ and $156_N$ is impregnated with a test substance, selected to determine the concentration of a selected substance in the fluid or the value of a selected property of the fluid.

One end of each of containers $152_1$, $152_2$, $152_3$, $152_4$, $152_5$ and $152_N$ is entirely or partially open, in order to allow the user to let the fluid into the container. Each of containers $152_1$, $152_2$, $152_3$, $152_4$, $152_5$ and $152_N$ can be closed by a matching stopper (not shown), in order to allow the user to shake the container and for the reaction between the test substance and the fluid to take place. Alternatively, the stoppers of containers $152_1$, $152_2$, $152_3$, $152_4$, $152_5$ and $152_N$ are part of a single body.

Test sub-sections $156_1$, $156_2$, $156_3$, $156_4$, $156_5$ and $156_N$ are transparent strips which are fastened to the inner wall of containers $152_1$, $152_2$, $152_3$, $152_4$, $152_5$ and $152_N$, respectively. Test sub-sections $156_1$, $156_2$, $156_3$, $156_4$, $156_5$ and $156_N$ are located adjacent to reference schemes $154_1$, $154_2$, $154_3$, $154_4$, $154_5$ and $154_N$, respectively.

The cross section of each of containers $152_1$, $152_2$, $152_3$, $152_4$, $152_5$ and $152_N$, along either the longitudinal axis or the transverse axis thereof, can be either variable or constant. This cross section can be in the form of rectangle, square, triangle, rhombus, parallelogram, trapezoid, quadrilateral, circle, annulus, ellipse, sector of a circle, freeform closed curve, and the like.

Each of containers $152_1$, $152_2$, $152_3$, $152_4$, $152_5$ and $152_N$ is made of a polymer, glass, timber, dry clay, ceramic, masonry, metal, and the like, having at least one transparent portion. If the container is opaque, then that portion of the container which covers a test sub-section, is enhanced by a transparent property or is made of a transparent material. Hence, the user can compare the color of a test sub-section with the colors of the respective reference colored sub-sections.

When the test substance of a test sub-section reacts with the fluid, the color of the test sub-section changes to a color substantially similar to the color of one of the reference colored sub-sections in the respective reference scheme. The user, then determines the value of the selected property of the fluid or the concentration of the selected substance in the fluid, by matching the new color of the test sub-section, with the color of one of the reference colored sub-sections.

With reference to FIG. 2B, containers $152_2$, $152_3$ and $152_N$ include reference schemes $154_2$, $154_3$ and $154_N$, respectively. Reference scheme $154_2$ includes reference colored sub-sections $154_{2,1}$, $154_{2,2}$, $154_{2,3}$, $154_{2,4}$ and $154_{2,N}$. Reference scheme $154_3$ includes reference colored sub-sections $154_{3,1}$, $154_{3,2}$, $154_{3,3}$, $154_{3,4}$ and $154_{3,N}$. Reference scheme $154_N$ includes reference colored sub-sections $154_{N,1}$, $154_{N,2}$, $154_{N,3}$, $154_{N,4}$ and $154_{N,N}$.

The fluid which is to be tested, is poured in containers $152_2$, $152_3$ and $152_N$. The test substances in test sub-sections $156_2$, $156_3$ and $156_N$ react with the fluid and the color of each of test sub-sections $156_2$, $156_3$ and $156_N$ in each container changes to the color of one of the reference colored sub-sections in the respective reference scheme. In the example set forth in FIG. 2B, container $152_2$ is designated to test the concentration of nitrate in the fluid. The user matches the color of test sub-section $156_2$ with reference colored sub-section $154_{2,2}$ and determines that the concentration of nitrate in the fluid is 12 mg/l.

Container $152_3$ is designated to test for example, the concentration of lead in the fluid. Reference colored sub-sections $154_{3,1}$, $154_{3,2}$, $154_{3,3}$, $154_{3,4}$ and $154_{3,N}$ designate lead concentrations of 0.0122, 0.0124, 0.0126, 0.0128 and 0.0130 mg/l, respectively, in the fluid. The user matches the color of test sub-section $156_3$ with reference colored sub-section $154_{3,4}$ and thus, determines that the concentration of lead in the fluid is 0.0128 mg/l.

Container $152_N$ is designated to test the concentration of sodium in the fluid. The user matches the color of test sub-section $156_N$ with reference colored sub-section $154_{N,1}$ and thus, determines that the concentration of sodium in the fluid is 16 mg/l.

Figure 3:
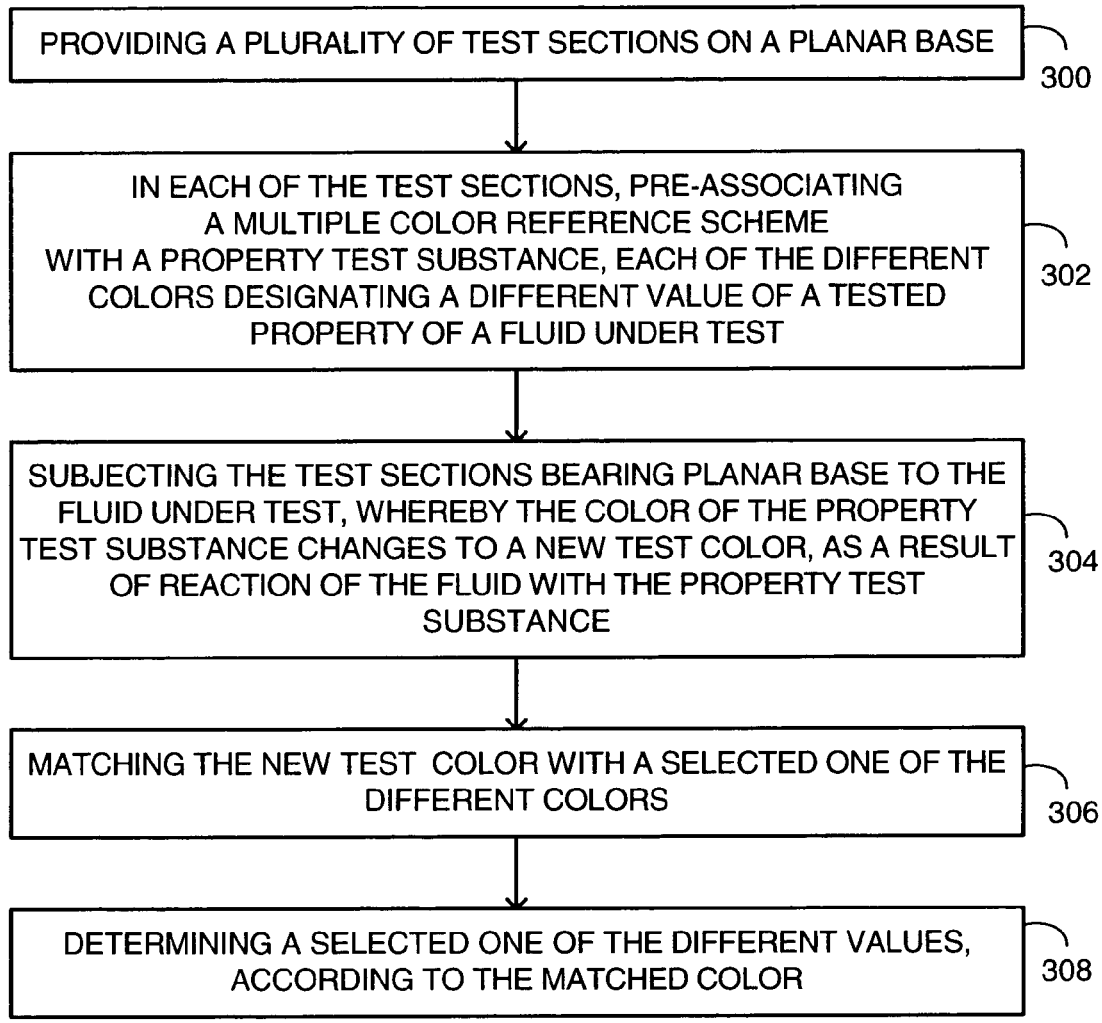
FIG. 3 is a schematic illustration of a method for determining a quantitative property of a fluid, operative in accordance with a further embodiment of the disclosed technique.

Reference is now made to FIG. 3, which is a schematic illustration of a method for determining a quantitative property of a fluid, operative in accordance with a further embodiment of the disclosed technique. In procedure 300, a plurality of test sections are provided on a planar base. With reference to FIG. 1A, test sections $102_1$, $102_2$, $102_3$, $102_4$, $102_5$ and $102_N$ are provided to test card 100.

In procedure 302, a multiple color reference scheme is pre-associated with a property test substance in each of the test sections, wherein each of the different colors designates a different value of a tested property of a fluid under test. With reference to FIG. 1A, reference schemes $106_1$, $106_2$, $106_3$, $106_4$, $106_5$ and $106_N$ of fluid testing device 100, are placed adjacent to test sub-sections $108_1$, $108_2$, $108_3$, $108_4$, $108_5$ and $108_N$, respectively. Each of test sub-sections $108_1$, $108_2$, $108_3$, $108_4$, $108_5$ and $108_N$ includes a selected test substance, to test the level of another substance in a fluid. For example, reference scheme $106_N$ is placed adjacent to test sub-section $108_N$. Reference scheme $106_N$ is colored in different shades of blue, as illustrated by reference colored sub-sections $106_{N,1}$, $106_{N,2}$, $106_{N,3}$, $106_{N,4}$ and $106_{N,N}$. Reference scheme $106_N$ is employed to determine the concentration of sodium and each of the reference colored sub-sections $106_{N,1}$, $106_{N,2}$, $106_{N,3}$, $106_{N,4}$ and $106_{N,N}$ designates a different sodium concentration in the fluid.

In procedure 304, the test sections bearing planar base is subjected to the fluid under test, whereby the color of the property test substance changes to a new test color, as a result of reaction of the fluid with the property test substance. With reference to FIGS. 1A and 1B, fluid testing device 100 is immersed in fluid 112, whereby fluid 112 reacts with the test substance included in test sub-section $108_N$ and the color of test sub-section $108_N$ (and the fluid which was absorbed by test sub-section $108_N$), changes to a new color.

In procedure 306, the new test color is matched with a selected one of the different colors. With reference to FIG. 1C, the user matches the color of test sub-section $108_N$ with reference colored sub-section $106_{N,1}$.

In procedure 308, a selected one of the different values is determined, according to the matched color. With reference to FIG. 1C, the user determines that the concentration of sodium (i.e., the property under test) in the fluid, is 16 mg/l.

Figure 4:
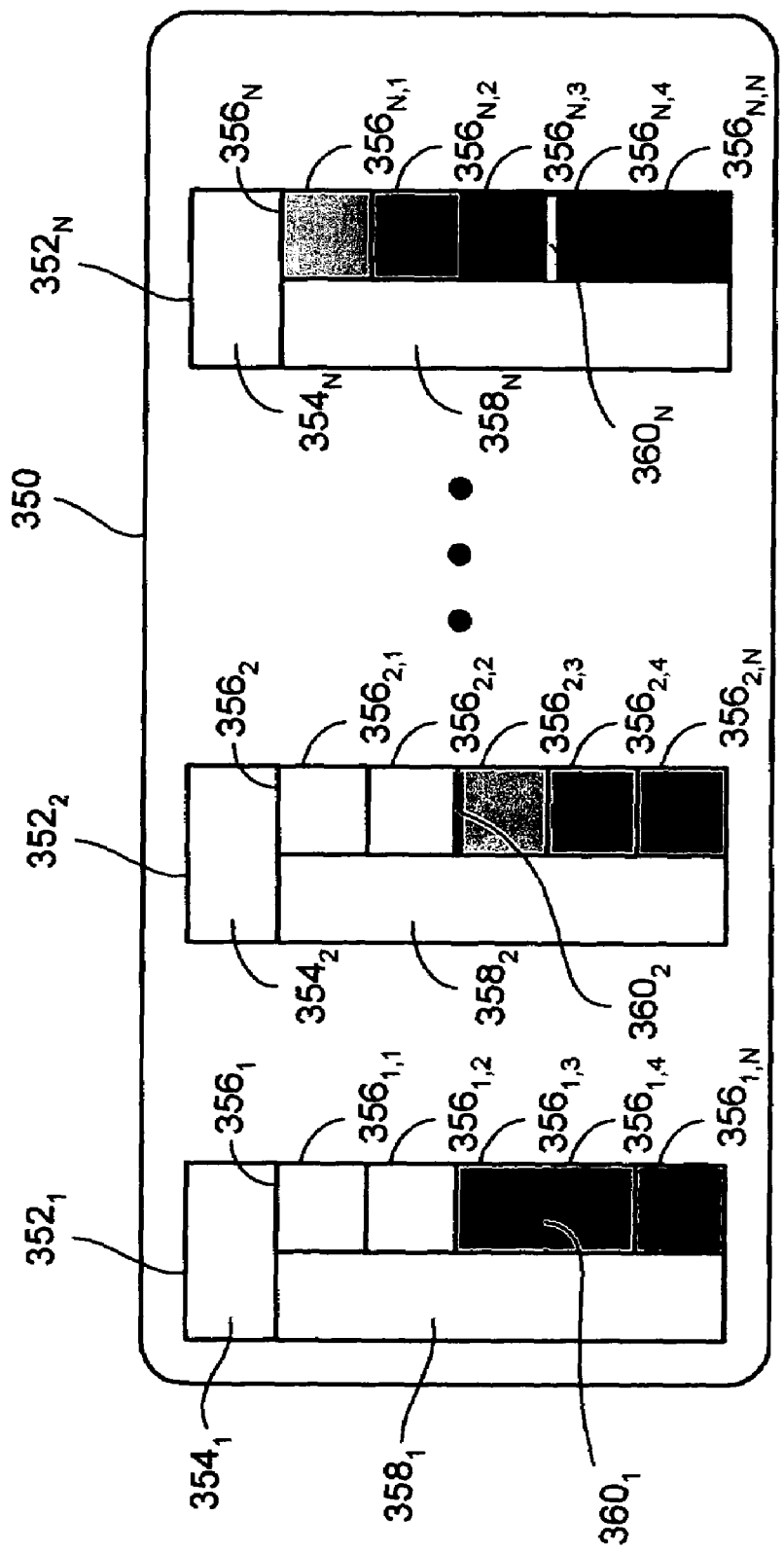
FIG. 4 is a schematic illustration of a fluid testing device, constructed and operative in accordance with another embodiment of the disclosed technique.

Reference is now made to FIG. 4, which is a schematic illustration of a fluid testing device, generally referenced 350, constructed and operative in accordance with another embodiment of the disclosed technique. Fluid testing device 350 includes a plurality of test sections $352_1$, $352_2$ and $352_N$. Test section $352_1$ includes a label section $354_1$, a reference scheme $356_1$ and a test sub-section $358_1$. Reference scheme $356_1$ includes a plurality of reference colored sub-sections $356_{1,1}$, $356_{1,2}$, $356_{1,3}$, $356_{1,4}$ and $356_{1,N}$ and a limit line $360_1$.

Test section $352_2$ includes a label section $354_2$, a reference scheme $356_2$ and a test sub-section $358_2$. Reference scheme $356_2$ includes a plurality of reference colored sub-sections $356_{2,1}$, $356_{2,2}$, $356_{2,3}$, $356_{2,4}$ and $356_{2,N}$ and a limit line $360_2$. Test section $352_N$ includes a label section $354_N$, a reference scheme $356_N$ and a test sub-section $358_N$. Reference scheme $356_N$ includes a plurality of reference colored sub-sections $356_{N,1}$, $356_{N,2}$, $356_{N,3}$, $356_{N,4}$ and $356_{N,N}$ and a limit line $360_N$.

Limit line $360_1$ is located between reference colored sub-sections $356_{1,3}$ and $356_{1,4}$. Limit line $360_2$ is located between reference colored sub-sections $356_{2,2}$ and $356_{2,3}$. Limit line $360_N$ is located between reference colored sub-sections $356_{N,3}$ and $356_{N,4}$.

Each limit line indicates to the user, that if the color of a test sub-section matches the color of one of the reference colored sub-sections which are located below the limit line, then the fluid under test, according to the tested property, is unacceptable for use. For example, if test section $352_1$ is employed to test the pH level of the fluid, and the color of test sub-section $358_1$ after immersion of fluid testing device 350 in the fluid, matches the color of reference colored sub-section $356_{1,4}$ or $356_{1,N}$, then the user determines that in both cases, the pH is below the allowable limit and thus the fluid is unacceptable for use.

Alternatively, the limit line indicates to the user, that if the color of a test sub-section matches the color of one of the reference colored sub-sections which are located above the limit line, then the fluid under test, according to the tested property, is unacceptable for use. For example, if test section $352_2$ is employed to test the concentration of nitrate in the fluid, and the color of test sub-section $358_2$ after immersion of fluid testing device 350 in the fluid, matches the color of reference colored sub-section $356_{2,1}$ or $356_{2,2}$, then the user determines that in both cases, the nitrate concentration is above the allowable limit and thus the fluid is unacceptable for use.

Figure 5A:
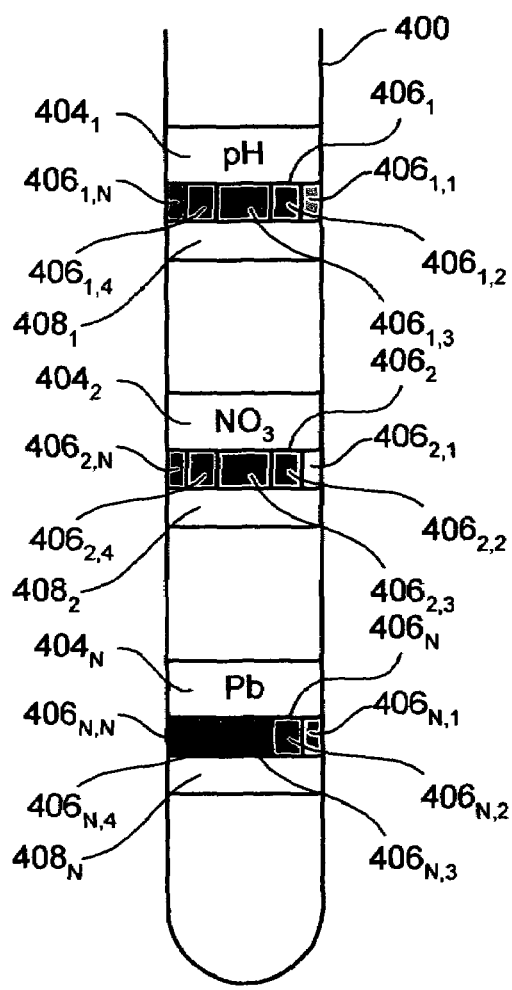
FIG. 5A is a schematic illustration of a container, constructed and operative in accordance with a further embodiment of the disclosed technique.
Figure 5B:
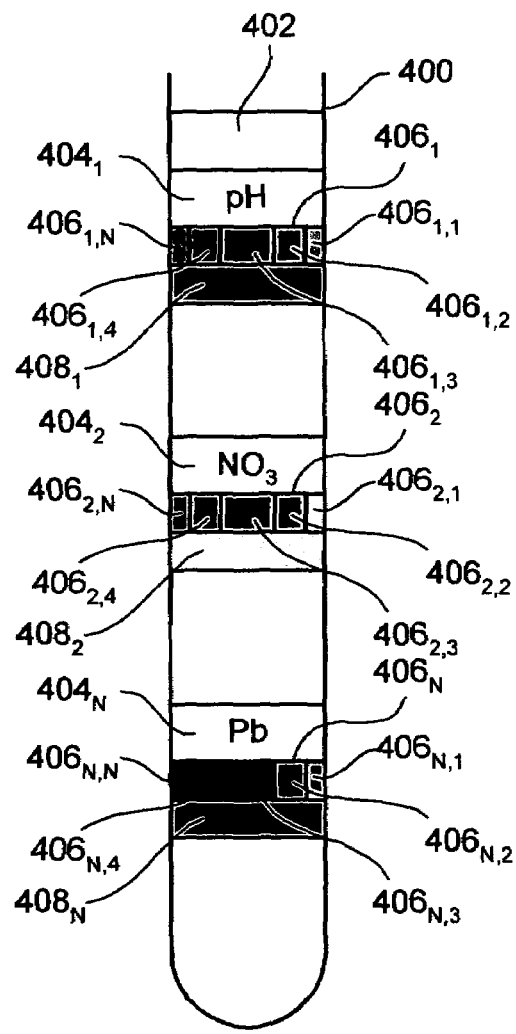
FIG. 5B is a schematic illustration of the container of FIG. 5A, after pouring a fluid in the container, wherein the fluid has reacted with different test substances.

Reference is now made to FIGS. 5A and 5B. FIG. 5A is a schematic illustration of a container, generally referenced 400, constructed and operative in accordance with a further embodiment of the disclosed technique. FIG. 5B is a schematic illustration of the container of FIG. 5A, after pouring a fluid in the container, wherein the fluid has reacted with different test substances. Container 400 includes a plurality of label sections $404_1$, $404_2$ and $404_N$, a plurality of reference schemes $406_1$, $406_2$ and $406_N$, and a plurality of test sub-sections $408_1$, $408_2$ and $408_N$.

Reference scheme $406_1$ includes a plurality of reference colored sub-sections $406_{1,1}$, $406_{1,2}$, $406_{1,3}$, $406_{1,4}$ and $406_{1,N}$. Reference scheme $406_2$ includes a plurality of reference colored sub-sections $406_{2,1}$, $406_{2,2}$, $406_{2,3}$, $406_{2,4}$ and $406_{2,N}$. Reference scheme $406_N$ includes a plurality of reference colored sub-sections $406_{N,1}$, $406_{N,2}$, $406_{N,3}$, $406_{N,4}$ and $406_{N,N}$.

Each of the label sections $404_1$, $404_2$ and $404_N$ is printed on an inner wall of container 400, on an outer wall thereof or within the wall of container 400. Alternatively, each of the label sections $404_1$, $404_2$ and $404_N$ is in form of a transparent or an opaque pressure sensitive tape, which is adhered either to the inner wall of container 400, or to the outer wall thereof.

Reference schemes $406_1$, $406_2$ and $406_N$ are located below label sections $404_1$, $404_2$ and $404_N$, respectively. Each of the reference schemes $406_1$, $406_2$ and $406_N$ is printed on an inner wall of container 400, on an outer wall thereof or within the wall of container 400. Alternatively, each of the label sections $406_1$, $406_2$ and $406_N$ is in form of a transparent or an opaque pressure sensitive tape, which is adhered either to the inner wall of container 400, or to the outer wall thereof. Alternatively, reference schemes $406_1$, $406_2$ and $406_N$ are located above label sections $404_1$, $404_2$ and $404_N$, respectively.

Each of test sub-sections $408_1$, $408_2$ and $408_N$ is a transparent strip which is impregnated with a test substance, wherein the transparent strip is fastened to the inner wall of container 400. Alternatively, each of test sub-sections $408_1$, $408_2$ and $408_N$ is a test substance in the form of a powder, which coats the inner wall of container 400. Test sub-sections $408_1$, $408_2$ and $408_N$ are located below reference schemes $406_1$, $406_2$ and $406_N$, respectively. Test sub-sections $408_1$, $408_2$ and $408_N$ are located substantially adjacent to reference schemes $406_1$, $406_2$ and $406_N$, respectively. Alternatively, test sub-sections $408_1$, $408_2$ and $408_N$ are located above reference schemes $406_1$, $406_2$ and $406_N$, respectively.

With reference to FIG. 5B, fluid 402 which is poured in container 400, fluid 402 reacts with test sub-sections $408_1$, $408_2$ and $408_N$ and as a result of the reaction, the color of fluid 402 in the vicinity of each of the test sub-sections $408_1$, $408_2$ and $408_N$, changes. The user, then determines the value of each property of fluid 402, or the concentration of a substance in fluid 402, by matching the color of fluid 402 in the vicinity of test sub-sections $408_1$, $408_2$ and $408_N$, with the color of one of the reference colored sub-sections of reference schemes $406_1$, $406_2$ and $406_N$, respectively.

It is noted that after performing a fluid test, test sub-sections $408_1$, $408_2$ and $408_N$ can be removed from the inner wall of container 400 and a new set of test sections applied to the inner wall of container 400, thereby allowing the user to perform a new fluid test, by employing container 400 once again. Alternatively, the user can dispose of the container after performing a test and use another container for performing a new test. Each of the test sub-sections further includes a limit line, whereby the user can determine whether the fluid under test is acceptable for use according to a selected property, if the color of fluid after reaction, matches the color of one of the reference colored sub-sections, which is located either to the right or to the left of the limit line.

It is noted that different combinations of the relative locations of a label section, the respective reference scheme and the respective test sub-section, can be selected. Hence, the combinations described above are not exhaustive and other combinations are possible.

Figure 6A:
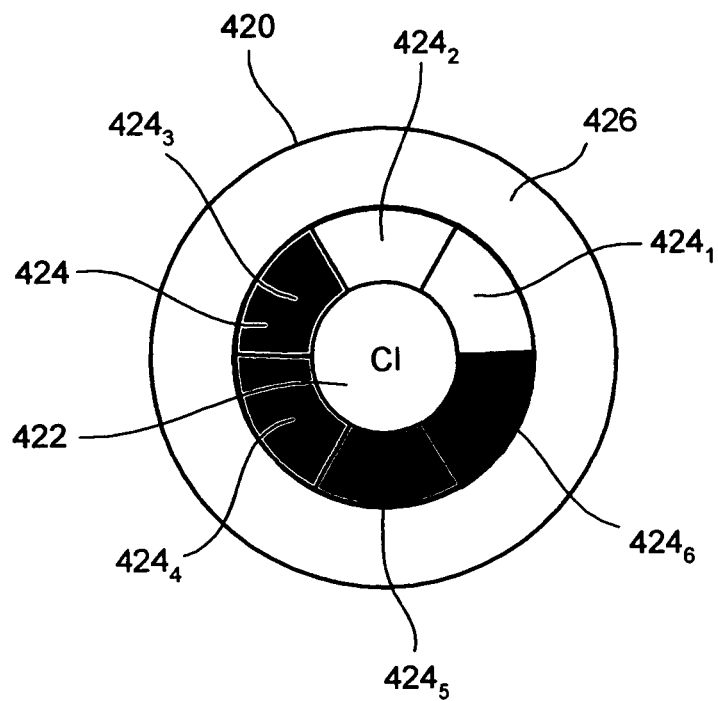
FIG. 6A is a schematic illustration of a test section, constructed and operative in accordance with another embodiment of the disclosed technique.
Figure 6B:
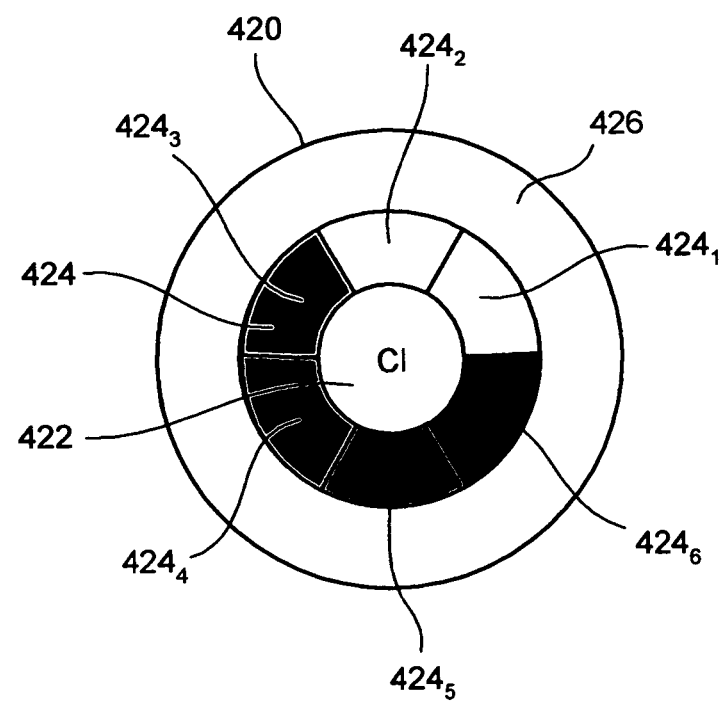
FIG. 6B is a schematic illustration of the test section of FIG. 6A, after a reaction of the test substance of the test sub-section with a fluid.

Reference is now made to FIGS. 6A and 6B. FIG. 6A is a schematic illustration of a test section, generally referenced 420, constructed and operative in accordance with another embodiment of the disclosed technique. FIG. 6B is a schematic illustration of the test section of FIG. 6A, after a reaction of the test substance of the test sub-section with a fluid.

With reference to FIG. 6A, test section 420 includes a label 422, a reference scheme 424 and a test sub-section 426. Reference scheme 424 includes a plurality of reference colored sub-sections $424_1$, $424_2$, $424_3$, $424_4$, $424_5$ and $424_6$. Test section 420 is in form of a circle. Label 422 is in form of a circle within test section 420. Reference scheme 424 is in form of an annulus around label 422. Each of reference colored sub-sections $424_1$, $424_2$, $424_3$, $424_4$, $424_5$ and $424_6$ is a sector of the annulus of reference scheme 424.

Test sub-section 426 is in form of an annulus surrounding reference scheme 424. Test sub-section 426 is impregnated with a selected test substance, in order to determine the concentration of a substance or the value of a property in the fluid. According to the example set forth in FIG. 6A, test sub-section 426 is impregnated with a test substance to determine the concentration of chlorine. The centers of label 422, reference scheme 424 and test sub-section 426, lie at substantially the same point.

With reference to FIG. 6B, test sub-section 426 exhibits a color which matches the color of reference colored sub-section $424_2$. Thus, the user determines that the concentration of chlorine in the fluid is for example, 0.5 mg/l. It is noted that any geometric shape can be used for a test section, including a rectangle, an ellipse, abstract shapes, known trade marks, and the like.

Figure 7:
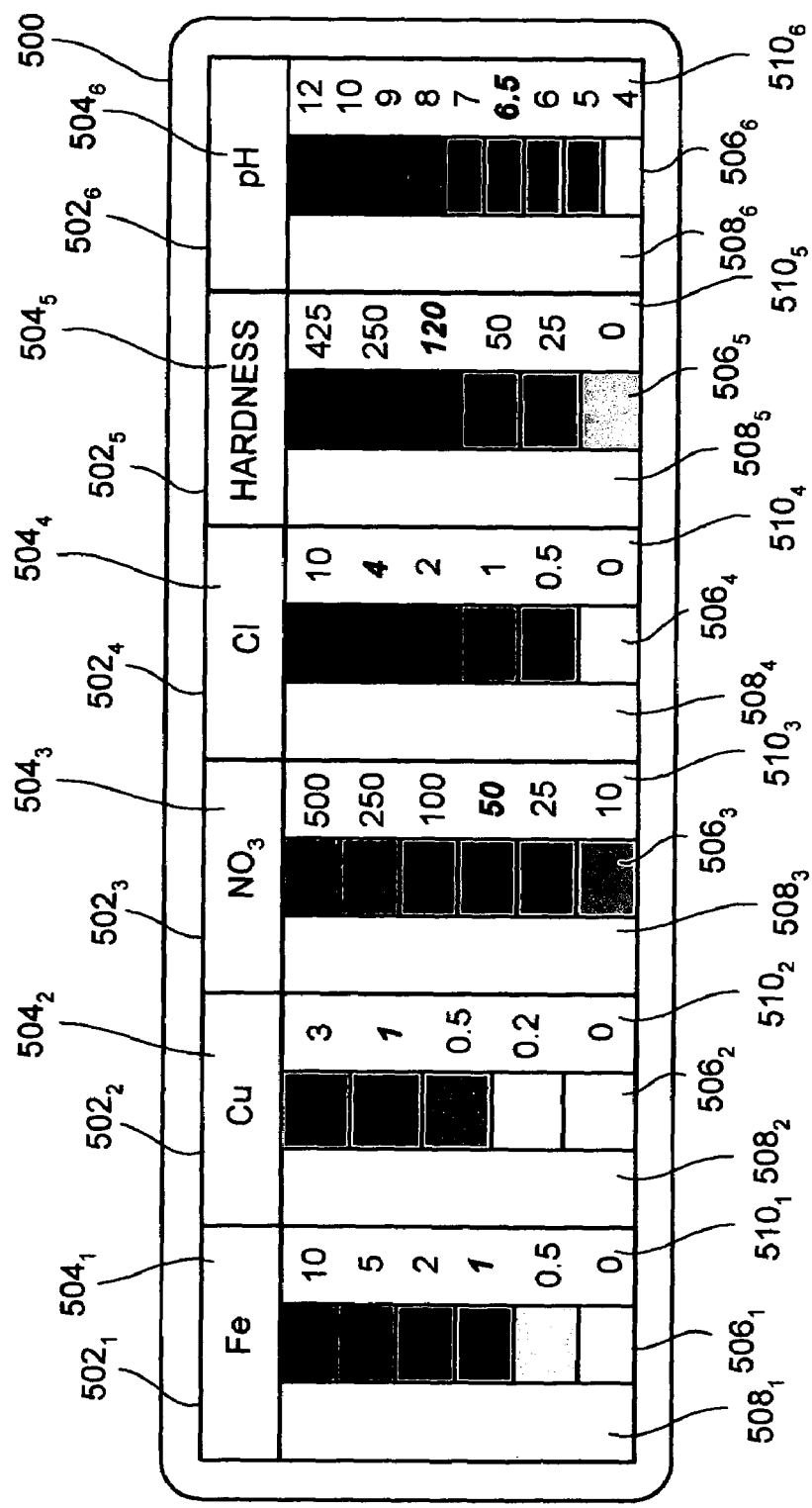
FIG. 7 is a schematic illustration of a fluid testing device, constructed and operative in accordance with a further embodiment of the disclosed technique.

Reference is now made to FIG. 7, which is a schematic illustration of a fluid testing device, generally referenced 500, constructed and operative in accordance with a further embodiment of the disclosed technique. Fluid testing device 500 includes a plurality of test sections $502_1$, $502_2$, $502_3$, $502_4$, $502_5$ and $502_6$. Test sections $502_1$, $502_2$, $502_3$, $502_4$, $502_5$ and $502_6$ include label sections $504_1$, $504_2$, $504_3$, $504_4$, $504_5$ and $504_6$, reference schemes $506_1$, $506_2$, $506_3$, $506_4$, $506_5$ and $506_6$, test sub-sections $508_1$, $508_2$, $508_3$, $508_4$, $508_5$ and $508_6$, and value indicating sections $510_1$, $510_2$, $510_3$, $510_4$, $510_5$ and $510_6$, respectively.

Each reference scheme further includes a plurality of reference colored sub-sections, each of which is in a different hue. A number is printed adjacent to each reference colored sub-section in each value indicating section. The material and geometry of fluid testing device 500 is similar to those of fluid testing device 100, as described herein above in connection with FIG. 1A.

Test sections $502_1$, $502_2$, $502_3$, $502_4$, $502_5$ and $502_6$ are designated for testing the concentration of iron (Fe), copper (Cu), nitrate ($NO_3$), chlorine (Cl), and the hardness and pH of water, respectively. The numbers in each value indicating section represent different concentrations of the respective substance or different values of the respective parameter in the water under test.

Thus, the user reads the concentration of the substance or the value of the parameter, after comparing the color of a test sub-section with the respective reference scheme and determining the reference colored sub-section which matches the color of the test sub-section. One of the numbers in each value indicating section is printed in a different style than the rest, thereby indicating the allowable concentration of a substance in water, or the allowable hardness or pH of water, according to a standard. For example, this number can be printed in bold, italics, be underlined, in a different color, in a different font, in a different size, and the like. It is noted that other properties of water can be determined, such as total alkalinity, and the like.

It will be appreciated by persons skilled in the art that the disclosed technique is not limited to what has been particularly shown and described here in above. Rather the scope of the disclosed technique is defined only by the claims which follow.

The invention claimed is:

1. An integrated, multi-test, immersable test strip-type fluid testing device for simultaneously determining the value of each of a plurality of properties of a fluid to be tested, the fluid testing device comprising:
   a test substrate; and
   a plurality of test sections, located on said test substrate, each of said test sections including:
     a test sub-section which exhibits a reaction color according to said value, as a result of reaction of a reagent with said fluid, said reagent being impregnated within said test sub-section prior to testing; and
     a reference section located adjacent to said test sub-section, said reference section including a plurality of different reference colors and being arranged such that each of said plurality of reference colors is situated adjacent to and in contact with said test sub-section, wherein said test sub-section substantially encompasses said entire reference section having said plurality of different reference colors, such that, when said test sub-section exhibits said reaction color in accordance with a fluid property value, said value is indicated by a matching one of said reference colors which lies against said test sub-section reaction color, so as to become substantially visually merged therewith, said device enabling fluid analysis of the test fluid by a self-contained, one-step procedure of immersion of the entire strip including both said test sub-section and said reference section, reaction during immersion and color reading of said reaction results upon retrieval from the test fluid, wherein reading of said indicated value in each test sub-section is performed by visually matching said test sub-section reaction color with said substantially visually merged one of said different reference colors due to self-alignment therebetween, such that said indicated value of each of the plurality of fluid properties can be simply read in a straight forward matching process with improved accuracy in simultaneous and immediate fashion, without requiring the physical alignment of said test sub-section reaction color with said reference colors, said indicated value of each of the plurality of multi-test fluid properties being provided in a recordable form, thereby enabling review of an entire set of said reaction results by summary inspection, wherein said plurality of multi-test fluid properties forms a group consisting essentially of pH, total hardness, nitrate, nitrite, free chlorine and copper.

2. The fluid testing device according to claim 1, wherein said test section further comprises a label respective of a property of said fluid.

3. The fluid testing device according to claim 1, wherein each of said properties is a concentration of a different substance in said fluid.

4. The fluid testing device according to claim 1, wherein said device is capable of testing fluids selected from the group consisting of:
water;
liquid fuel; and
crude oil.

5. The fluid testing device according to claim 1, wherein said test substrate is made of a material selected from the list consisting of:
flexible polymer;
rigid polymer;
fabricated materials;
glass;
paper;
plastic coated paper;
cardboard;
timber;
dry clay;
ceramic;
masonry;
leather;
textile; and
metal.

6. The fluid testing device according to claim 1, wherein said test substrate is in the form of a sheet.

7. The fluid testing device according to claim 6, wherein the geometry of said sheet is selected from the list consisting of:
rectangle;
square;
triangle;
rhombus;
parallelogram;
trapezoid;
quadrilateral;
circle;
annulus;
ellipse;
sector of a circle; and
freeform closed curve.

8. The fluid testing device according to claim 6, wherein the form of said sheet is selected from the list consisting of:
flat;
rolled;
folded;
twisted;
convex; and
concave.

9. The fluid testing device according to claim 1, wherein said different reference colors are of the same hue, and wherein each of said reference colors are of different saturation levels and different brightness levels.

10. The fluid testing device according to claim 1, wherein at least one of said different reference colors designating an acceptable value of a property of said fluid, is separated by a limit line, from at least another one of said different reference colors designating an unacceptable value of said property.

11. The fluid testing device according to claim 1, wherein said test section further comprises a value indicating section, said value indicating section includes a plurality of numbers, each of said numbers is located adjacent to a respective reference color, each of said numbers represents a selected value of a property of said fluid.

12. The fluid testing device according to claim 11, wherein a selected one of said numbers is represented in a different style, thereby separating at least one number which designates an acceptable value of said property, from at least another number which designates an unacceptable value of said property.

13. The fluid testing device according to claim 12, wherein said different style is selected from the list consisting of:
bold;
italics;
underlined;
color;
font; and
size.

14. The fluid testing device of claim 1 further comprising:
a container, having at least a transparent portion, within which said test substrate is disposed.

15. The fluid testing device according to claim 14, further comprising a stopper for closing an at least partially open end of said container.

16. The fluid testing device according to claim 14, wherein said container is made of a material selected from the list consisting of:
polymer;
glass;
timber;
dry clay;

ceramic;
masonry; and
metal.

17. The fluid testing device according to claim 14, wherein the cross section of said container is selected from the list consisting of:
rectangle;
square;
triangle;
rhombus;
parallelogram;
trapezoid;
quadrilateral;
circle;
annulus;
ellipse;
sector of a circle; and
freeform closed curve.

18. The fluid testing device according to claim 14, wherein said container comprises a plurality of different labels respective of different ones of said properties, each of said different labels being located adjacent to a respective one of said test sections.

19. The fluid testing device according to claim 14, wherein each one of said test sections is attached to the inner wall of said container.

20. The fluid testing device according to claim 19, wherein said test section is replaced by an unused test section of the same kind, after testing said fluid.

21. The fluid testing device according to claim 14, wherein a reference section respective of a property of said fluid is in form of a circle, said different reference colors respective of said reference section are in form of sectors of said circle and a test section respective of said property, is in form of an annulus surrounding said circle.

22. The fluid testing device of claim 1 further comprising:
a plurality of containers, each container having,
at least a transparent portion; and
a test substrate disposed therein.

23. The fluid testing device according to claim 22, wherein said containers are part of a solid body.

24. The fluid testing device according to claim 22, wherein each of said containers is a separate body, and wherein said containers are attached together by an adhesive or at least one fastener or welding.

25. The fluid testing device according to claim 22, further comprising an at least partially open end of each of said containers and a stopper for closing an at least partially open end of each of said containers.

26. The fluid testing device according to claim 25, wherein said stoppers are part of a body.

27. A method for determining the value of each of a plurality of multi-test properties of a fluid, the method comprising the steps of:
providing a plurality of test sections on a test substrate;
pre-associating a multiple color reference scheme with a property test substance which has been impregnated within each of a respective one of said test sections prior to testing, such that each reference color of said reference scheme is situated adjacent to and in contact with said property test substance on said test section, wherein said test section substantially encompasses said entire reference scheme having said multiple reference colors;
immersing said test substrate in said fluid, the property test substance on each test section exhibiting, in accordance with a value of said fluid property, a test reaction color that matches one of the reference colors located on its adjacent reference scheme, so as to become substantially visually merged therewith;
identifying said exhibited test reaction color of said property test substance that matches a selected one of different reference colors of said multiple color reference scheme, without requiring the physical alignment of said test sub-section with said reference colors; and
determining a respective one of said values according to the outcome of said identifying step, by visually matching said exhibited test reaction color with one of said different reference colors due to self-alignment therebetween,
said determined respective one of said values being provided in a recordable form
thereby enabling review of an entire set of said reaction results by summary inspection,
wherein said plurality of multi-test fluid properties forms a group consisting essentially of pH, total hardness, nitrate and nitrite.

28. The method according to claim 27, wherein said determining step further comprises reading a selected one of a plurality of numbers, said selected number designates said value, and
wherein each of said numbers is located adjacent to a respective one of said different colors.

29. A method for determining the value of each of a plurality of multi-test properties of a fluid, the method comprising the steps of:
providing a plurality of test sections, each located on the inner wall of a respective one of a plurality of containers;
pre-associating a multiple color reference scheme with a property test substance which has been impregnated within each of a respective one of said test sections prior to testing, such that each reference color of said reference scheme is situated adjacent to and in contact with said property test substance on said test section, wherein said test section substantially encompasses said entire reference scheme having said multiple reference colors;
subjecting said test sections to said fluid, the property test substance on each test section exhibiting, in accordance with a value of said fluid property and upon contact with said fluid, a test reaction color that matches one of the reference colors located on its adjacent reference scheme, so as to become substantially visually merged therewith;
identifying said exhibited test reaction color of said property test substance that matches a selected one of different reference colors of said multiple color reference scheme, without requiring the physical alignment of said test sub-section with said reference colors; and
determining a respective one of said values according to the outcome of said identifying step, by visually matching said exhibited test reaction color with one of said different reference colors due to self-alignment therebetween,
said determined respective one of said values being provided in a recordable form
thereby enabling review of an entire set of said reaction results by summary inspection,
wherein said plurality of multi-test fluid properties forms a group consisting essentially of pH, total hardness, free chlorine and total chlorine.

30. The fluid testing device according to claim 22, wherein said containers are constructed as separate cavities within a single body.

31. An integrated, multi-test, immersable test strip-type fluid testing device for simultaneously determining the value of each of a plurality of properties of a fluid to be tested, the fluid testing device comprising:
   a test substrate; and
   a plurality of test sections, located on said test substrate, each of said test sections including:
      a test sub-section which exhibits a reaction color according to said value, as a result of reaction of a reagent with said fluid, said reagent being impregnated within said test sub-section prior to testing; and
      a reference section located adjacent to said test sub-section, said reference section including a plurality of different reference colors and being arranged such that each of said plurality of reference colors is situated adjacent to and in contact with said test sub-section, wherein said test sub-section substantially encompasses said entire reference section having said plurality of different reference colors, such that, when said test sub-section exhibits said reaction color in accordance with a fluid property value, said value is indicated by a matching one of said reference colors which lies against said test sub-section reaction color, so as to become substantially visually merged therewith,
   said device enabling fluid analysis of the test fluid by a self-contained, one-step procedure of immersion of the entire strip including both said test sub-section and said reference section, reaction during immersion and color reading of said reaction results upon retrieval from the test fluid,
   wherein reading of said indicated value in each test sub-section is performed by visually matching said test sub-section reaction color with said substantially visually merged one of said different reference colors due to self-alignment therebetween,
   such that said indicated value of each of the plurality of fluid properties can be simply read in a straight forward matching process with improved accuracy in simultaneous and immediate fashion,
   without requiring the physical alignment of said test sub-section reaction color with said reference colors,
   said indicated value of each of the plurality of multi-test fluid properties being provided in a recordable form,
   thereby enabling review of an entire set of said reaction results by summary inspection,
   wherein said plurality of multi-test fluid properties forms a group consisting essentially of pH, total hardness, free chlorine, total chlorine and at least one of the subgroup of lead, zinc, iron and copper.

32. An integrated, multi-test, immersable test strip-type fluid testing device for simultaneously determining the value of each of a plurality of properties of a fluid to be tested, the fluid testing device comprising:
   a test substrate; and
   a plurality of test sections, located on said test substrate, each of said test sections including:
      a test sub-section which exhibits a reaction color according to said value, as a result of reaction of a reagent with said fluid, said reagent being impregnated within said test sub-section prior to testing; and
      a reference section located adjacent to said test sub-section, said reference section including a plurality of different reference colors and being arranged such that each of said plurality of reference colors is situated adjacent to and in contact with said test sub-section, wherein said test sub-section substantially encompasses said entire reference section having said plurality of different reference colors, such that, when said test sub-section exhibits said reaction color in accordance with a fluid property value, said value is indicated by a matching one of said reference colors which lies against said test sub-section reaction color, so as to become substantially visually merged therewith,
   said device enabling fluid analysis of the test fluid by a self-contained, one-step procedure of immersion of the entire strip including both said test sub-section and said reference section, reaction during immersion and color reading of said reaction results upon retrieval from the test fluid,
   wherein reading of said indicated value in each test sub-section is performed by visually matching said test sub-section reaction color with said substantially visually merged one of said different reference colors due to self-alignment therebetween,
   such that said indicated value of each of the plurality of fluid properties can be simply read in a straight forward matching process with improved accuracy in simultaneous and immediate fashion,
   without requiring the physical alignment of said test sub-section reaction color with said reference colors,
   said indicated value of each of the plurality of multi-test fluid properties being provided in a recordable form,
   thereby enabling review of an entire set of said reaction results by summary inspection,
   wherein said plurality of multi-test fluid properties forms a group consisting essentially of pH, total alkalinity, total hardness, nitrate, and nitrite.

33. An integrated, multi-test, immersable test strip-type fluid testing device for simultaneously determining the value of each of a plurality of properties of a fluid to be tested, the fluid testing device comprising:
   a test substrate; and
   a plurality of test sections, located on said test substrate, each of said test sections including:
      a test sub-section which exhibits a reaction color according to said value, as a result of reaction of a reagent with said fluid, said reagent being impregnated within said test sub-section prior to testing; and
      a reference section located adjacent to said test sub-section, said reference section including a plurality of different reference colors and being arranged such that each of said plurality of reference colors is situated adjacent to and in contact with said test sub-section, wherein said test sub-section substantially encompasses said entire reference section having said plurality of different reference colors, such that, when said test sub-section exhibits said reaction color in accordance with a fluid property value, said value is indicated by a matching one of said reference colors which lies against said test sub-section reaction color, so as to become substantially visually merged therewith,
   said device enabling fluid analysis of the test fluid by a self-contained, one-step procedure of immersion of the entire strip including both said test sub-section and said reference section, reaction during immersion and color reading of said reaction results upon retrieval from the test fluid, wherein reading of said indicated value in each test sub-section is performed by visually matching said test sub-section reaction color with said substantially visually merged one of said different reference colors due to self-alignment therebetween, such that said indicated value of each of the plurality of fluid properties can be simply read in a straight forward matching process with improved accuracy in simultaneous and immediate fashion, without requiring the physical alignment of said test sub-section reaction color with said reference colors, said indicated value of each of the plurality of multi-test fluid properties being provided in a recordable form, thereby enabling review of an entire set of said reaction results by summary inspection, wherein said plurality of multi-test fluid properties forms a group consisting essentially of pH, free chlorine and total alkalinity.

34. An integrated, multi-test, immersable test strip-type fluid testing device for simultaneously determining the value of each of a plurality of properties of a fluid to be tested, the fluid testing device comprising:

a test substrate; and a plurality of test sections, located on said test substrate, each of said test sections including:

a test sub-section which exhibits a reaction color according to said value, as a result of reaction of a reagent with said fluid, said reagent being impregnated within said test sub-section prior to testing; and a reference section located adjacent to said test sub-section, said reference section including a plurality of different reference colors and being arranged such that each of said plurality of reference colors is situated adjacent to and in contact with said test sub-section, wherein said test sub-section substantially encompasses said entire reference section having said plurality of different reference colors, such that, when said test sub-section exhibits said reaction color in accordance with a fluid property value, said value is indicated by a matching one of said reference colors which lies against said test sub-section reaction color, so as to become substantially visually merged therewith, said device enabling fluid analysis of the test fluid by a self-contained, one-step procedure of immersion of the entire strip including both said test sub-section and said reference section, reaction during immersion and color reading of said reaction results upon retrieval from the test fluid, wherein reading of said indicated value in each test sub-section is performed by visually matching said test sub-section reaction color with said substantially visually merged one of said different reference colors due to self-alignment therebetween, such that said indicated value of each of the plurality of fluid properties can be simply read in a straight forward matching process with improved accuracy in simultaneous and immediate fashion, without requiring the physical alignment of said test sub-section reaction color with said reference colors, said indicated value of each of the plurality of multi-test fluid properties being provided in a recordable form, thereby enabling review of an entire set of said reaction results by summary inspection, wherein said plurality of multi-test fluid properties forms a group consisting essentially of pH, total hardness, free chlorine, total chlorine, total alkalinity, nitrate, nitrite and at least one of the subgroup of lead, zinc, iron and copper.

35. An integrated, multi-test, immersable test strip-type fluid testing device for simultaneously determining the value of each of a plurality of properties of a fluid to be tested, the fluid testing device comprising:

a test substrate; and a plurality of test sections, located on said test substrate, each of said test sections including:

a test sub-section which exhibits a reaction color according to said value, as a result of reaction of a reagent with said fluid, said reagent being impregnated within said test sub-section prior to testing; and a reference section located adjacent to said test sub-section, said reference section including a plurality of different reference colors and being arranged such that each of said plurality of reference colors is situated adjacent to and in contact with said test sub-section, wherein said test sub-section substantially encompasses said entire reference section having said plurality of different reference colors, such that, when said test sub-section exhibits said reaction color in accordance with a fluid property value, said value is indicated by a matching one of said reference colors which lies against said test sub-section reaction color, so as to become substantially visually merged therewith, said device enabling fluid analysis of the test fluid by a self-contained, one-step procedure of immersion of the entire strip including both said test sub-section and said reference section, reaction during immersion and color reading of said reaction results upon retrieval from the test fluid, wherein reading of said indicated value in each test sub-section is performed by visually matching said test sub-section reaction color with said substantially visually merged one of said different reference colors due to self-alignment therebetween, such that said indicated value of each of the plurality of fluid properties can be simply read in a straight forward matching process with improved accuracy in simultaneous and immediate fashion, without requiring the physical alignment of said test sub-section reaction color with said reference colors, said indicated value of each of the plurality of multi-test fluid properties being provided in a recordable form, thereby enabling review of an entire set of said reaction results by summary inspection, wherein said plurality of multi-test fluid properties forms a group consisting essentially of free chlorine, total chlorine and at least one of the subgroup of lead, zinc, iron and copper.

36. An integrated, multi-test, immersable test strip-type fluid testing device for simultaneously determining the value of each of a plurality of properties of a fluid to be tested, the fluid testing device comprising:

a test substrate; and a plurality of test sections, located on said test substrate, each of said test sections including:

a test sub-section which exhibits a reaction color according to said value, as a result of reaction of a reagent with said fluid, said reagent being impregnated within said test sub-section prior to testing; and a reference section located adjacent to said test sub-section, said reference section including a plurality of different reference colors and being arranged such that each of said plurality of reference colors is situated adjacent to and in contact with said test sub-section, wherein said test sub-section substantially encompasses said entire reference section having said plurality of different reference colors, such that, when said test sub-section exhibits said reaction color in accordance with a fluid property value, said value is indicated by a matching one of said reference colors which lies against said test sub-section reaction color, so as to become substantially visually merged therewith, said device enabling fluid analysis of the test fluid by a self-contained, one-step procedure of immersion of the entire strip including both said test sub-section and said reference section, reaction during immersion and color reading of said reaction results upon retrieval from the test fluid, wherein reading of said indicated value in each test sub-section is performed by visually matching said test sub-section reaction color with said substantially visually merged one of said different reference colors due to self-alignment therebetween, such that said indicated value of each of the plurality of fluid properties can be simply read in a straight forward matching process with improved accuracy in simultaneous and immediate fashion, without requiring the physical alignment of said test sub-section reaction color with said reference colors, said indicated value of each of the plurality of multi-test fluid properties being provided in a recordable form, thereby enabling review of an entire set of said reaction results by summary inspection, wherein said plurality of multi-test fluid properties forms a group consisting essentially of total alkalinity, nitrate, nitrite and at least one of the subgroup of lead, zinc, iron and copper.

37. An integrated, multi-test, immersable test strip-type fluid testing device for simultaneously determining the value of each of a plurality of properties of a fluid to be tested, the fluid testing device comprising:

a test substrate; and a plurality of test sections, located on said test substrate, each of said test sections including:

a test sub-section which exhibits a reaction color according to said value, as a result of reaction of a reagent with said fluid, said reagent being impregnated within said test sub-section prior to testing; and a reference section located adjacent to said test sub-section, said reference section including a plurality of different reference colors and being arranged such that each of said plurality of reference colors is situated adjacent to and in contact with said test sub-section, wherein said test sub-section substantially encompasses said entire reference section having said plurality of different reference colors, such that, when said test sub-section exhibits said reaction color in accordance with a fluid property value, said value is indicated by a matching one of said reference colors which lies against said test sub-section reaction color, so as to become substantially visually merged therewith, said device enabling fluid analysis of the test fluid by a self-contained, one-step procedure of immersion of the entire strip including both said test sub-section and said reference section, reaction during immersion and color reading of said reaction results upon retrieval from the test fluid, wherein reading of said indicated value in each test sub-section is performed by visually matching said test sub-section reaction color with said substantially visually merged one of said different reference colors due to self-alignment therebetween, such that said indicated value of each of the plurality of fluid properties can be simply read in a straight forward matching process with improved accuracy in simultaneous and immediate fashion, without requiring the physical alignment of said test sub-section reaction color with said reference colors, said indicated value of each of the plurality of multi-test fluid properties being provided in a recordable form, thereby enabling review of an entire set of said reaction results by summary inspection, wherein said plurality of multi-test fluid properties forms a group consisting essentially of pH, total hardness, free chlorine, total chlorine, total alkalinity, and at least one of the subgroup of lead, zinc, iron and copper.

38. An integrated, multi-test, immersable test strip-type fluid testing device for simultaneously determining the value of each of a plurality of properties of a fluid to be tested, the fluid testing device comprising:

a test substrate; and a plurality of test sections, located on said test substrate, each of said test sections including:

a test sub-section which exhibits a reaction color according to said value, as a result of reaction of a reagent with said fluid, said reagent being impregnated within said test sub-section prior to testing; and a reference section located adjacent to said test sub-section, said reference section including a plurality of different reference colors and being arranged such that each of said plurality of reference colors is situated adjacent to and in contact with said test sub-section, wherein said test sub-section substantially encompasses said entire reference section having said plurality of different reference colors, such that, when said test sub-section exhibits said reaction color in accordance with a fluid property value, said value is indicated by a matching one of said reference colors which lies against said test sub-section reaction color, so as to become substantially visually merged therewith, said device enabling fluid analysis of the test fluid by a self-contained, one-step procedure of immersion of the entire strip including both said test sub-section and said reference section, reaction during immersion and color reading of said reaction results upon retrieval from the test fluid, wherein reading of said indicated value in each test sub-section is performed by visually matching said test sub-section reaction color with said substantially visually merged one of said different reference colors due to self-alignment therebetween, such that said indicated value of each of the plurality of fluid properties can be simply read in a straight forward matching process with improved accuracy in simultaneous and immediate fashion, without requiring the physical alignment of said test sub-section reaction color with said reference colors, said indicated value of each of the plurality of multi-test fluid properties being provided in a recordable form, thereby enabling review of an entire set of said reaction results by summary inspection, wherein said plurality of multi-test fluid properties forms a group consisting essentially of pH, total hardness, total alkalinity and at least one of the subgroup of free chlorine and total chlorine.

* * * * *